(12) United States Patent
Eifler et al.

(10) Patent No.: US 10,363,228 B2
(45) Date of Patent: Jul. 30, 2019

(54) TRANSDERMAL ADMINISTRATION OF MEMANTINE

(75) Inventors: René Eifler, Koblenz (DE); Michael Horstmann, Neuwied (DE); Regine Kaufmann, Neuwied (DE); Patrick Mohr, Bad Breisig (DE); Eric Galia, Aachen (DE); Wolfgang Prange, Grafschaft (DE); Stefan Buller, Baesweiler (DE); Klaus Pusecker, Korschenbroich (DE); Jan Stampfuss, Duesseldorf (DE); Susanne Stoelben, Cologne (DE)

(73) Assignees: LTS Lohmann Therapie-Systeme AG, Andernach (DE); Gruenenthal GmbH, Aachen (DE)

(*) Notice: Subject to any disclaimer, the term of this patent is extended or adjusted under 35 U.S.C. 154(b) by 89 days.

(21) Appl. No.: 13/162,604

(22) Filed: Jun. 17, 2011

(65) Prior Publication Data

US 2011/0313372 A1    Dec. 22, 2011

(30) Foreign Application Priority Data

Jun. 17, 2010    (DE) .................. 10 2010 024 105

(51) Int. Cl.
| | | |
|---|---|---|
| *A61F 13/00* | (2006.01) | |
| *A61M 35/00* | (2006.01) | |
| *A61N 1/30* | (2006.01) | |
| *A61K 9/70* | (2006.01) | |
| *A61K 31/13* | (2006.01) | |

(52) U.S. Cl.
CPC .......... *A61K 9/7053* (2013.01); *A61K 9/7061* (2013.01); *A61K 31/13* (2013.01)

(58) Field of Classification Search
None
See application file for complete search history.

(56) References Cited

U.S. PATENT DOCUMENTS

| | | | | |
|---|---|---|---|---|
| 4,336,243 A | * | 6/1982 | Sanvordeker | A61K 9/7069 424/449 |
| 4,615,699 A | * | 10/1986 | Gale | A61K 9/7084 424/448 |
| 4,781,924 A | * | 11/1988 | Lee | A61K 9/7084 424/449 |
| 5,230,898 A | * | 7/1993 | Horstmann | A61K 9/703 424/443 |

(Continued)

FOREIGN PATENT DOCUMENTS

| | | |
|---|---|---|
| JP | 2009-013171 A | 1/2009 |
| WO | WO89/09051 * | 10/1989 |

(Continued)

OTHER PUBLICATIONS

G. Lefèvre et al., Clinical Pharmacology & Therapeutics, 83(1), 2008, 106-114.
Verpackungs-Rundschau Apr. 2002, 83-84.

*Primary Examiner* — Bradley H Philips
(74) *Attorney, Agent, or Firm* — ProPat, L.L.C.; Cathy Moore (57) ABSTRACT

The invention relates to transdermal therapeutic systems (TTS) which include, as active ingredient, the NMDA receptor antagonist memantine or one of its physiologically compatible salts. The TTSs can be produced and used for treating diseases of the central nervous system.

23 Claims, 3 Drawing Sheets

(56) References Cited

U.S. PATENT DOCUMENTS

| | | | |
|---|---|---|---|
| 5,891,885 A * | 4/1999 | Caruso | A61K 31/00 514/289 |
| 6,183,770 B1 * | 2/2001 | Muchin | A61K 9/703 424/443 |
| 6,194,000 B1 | 2/2001 | Smith et al. | |
| 6,221,383 B1 * | 4/2001 | Miranda | A61F 13/0276 424/448 |
| 6,620,429 B1 * | 9/2003 | Muller | A61K 9/7061 424/443 |
| 6,638,528 B1 * | 10/2003 | Kanios | 424/449 |
| 6,743,211 B1 * | 6/2004 | Prausnitz | A61B 5/14514 424/449 |
| 6,746,689 B2 * | 6/2004 | Fischer | A61K 9/0014 424/447 |
| 6,770,295 B1 * | 8/2004 | Kreilgard | A61K 9/5078 424/449 |
| 7,175,853 B1 * | 2/2007 | Bracht | A61K 9/7069 424/443 |
| 7,291,620 B2 * | 11/2007 | Coburn et al. | 514/255.01 |
| 8,882,729 B2 * | 11/2014 | Horstmann | A61K 9/7084 424/449 |
| 9,833,418 B2 * | 12/2017 | Eifler | A61K 9/7061 |
| 2002/0016319 A1 | 2/2002 | Olney et al. | |
| 2003/0082225 A1 * | 5/2003 | Mason | 424/449 |
| 2003/0139698 A1 | 7/2003 | Hyson | |
| 2004/0013620 A1 * | 1/2004 | Klose et al. | 424/59 |
| 2004/0076648 A1 * | 4/2004 | Williams | A61K 9/0014 424/400 |
| 2004/0102525 A1 | 5/2004 | Kozachuk | |
| 2004/0202705 A1 * | 10/2004 | Xiong et al. | 424/449 |
| 2005/0202073 A1 * | 9/2005 | Jackson | A61K 9/7053 424/449 |
| 2005/0209218 A1 * | 9/2005 | Meyerson et al. | 514/220 |
| 2005/0245617 A1 * | 11/2005 | Meyerson et al. | 514/649 |
| 2006/0142398 A1 * | 6/2006 | Went et al. | 514/662 |
| 2006/0252788 A1 * | 11/2006 | Went et al. | 514/294 |
| 2007/0026054 A1 * | 2/2007 | Theobald | A61K 9/7092 424/448 |
| 2007/0098771 A1 * | 5/2007 | Audett | A61K 9/7061 424/449 |
| 2007/0128263 A1 * | 6/2007 | Gargiulo et al. | 424/449 |
| 2008/0026042 A1 * | 1/2008 | Reidenberg | A61K 9/7023 424/449 |
| 2008/0032965 A1 * | 2/2008 | Hirst et al. | 514/215 |
| 2008/0044461 A1 * | 2/2008 | Valia et al. | 424/449 |
| 2008/0107719 A1 * | 5/2008 | Likitlersuang | A61K 9/0009 424/449 |
| 2009/0246265 A1 * | 10/2009 | Stinchcomb | A61K 9/7061 424/449 |
| 2010/0028412 A1 * | 2/2010 | Asmussen | A61K 9/7084 424/449 |
| 2010/0028427 A1 * | 2/2010 | Yang et al. | 424/468 |
| 2012/0065599 A1 * | 3/2012 | Eifler | A61K 9/7061 604/290 |
| 2012/0245537 A1 * | 9/2012 | Horstmann | A61K 9/0014 604/290 |

FOREIGN PATENT DOCUMENTS

| | | |
|---|---|---|
| WO | WO 00/03716 A1 | 1/2000 |
| WO | WO 03/015699 A2 | 2/2003 |
| WO | WO 2004/009062 A2 | 1/2004 |
| WO | WO 2004/106275 A2 | 12/2004 |
| WO | WO 2005/072705 A1 | 8/2005 |
| WO | WO 2009/112167 A1 | 9/2009 |

* cited by examiner

TRANSDERMAL ADMINISTRATION OF MEMANTINE

CROSS-REFERENCE TO RELATED APPLICATIONS

This application claims priority to German Patent Application 10 2010 024 105.9 filed Jun. 17, 2010 which is hereby incorporated herein by reference in its entirety.

FIELD OF THE INVENTION

Transdermal therapeutic systems (TTSs) are provided which include, as active ingredient, the NMDA receptor antagonist memantine or one of its physiologically compatible salts. The TTSs can be produced and used for treating diseases of the central nervous system.

BACKGROUND OF THE INVENTION

According to the prior art, diseases of the central nervous system, more particularly dementias comprising mild to moderate forms of Alzheimer's disease, are treated by means of acetylcholinesterase inhibitors (e.g., donepezil). For the treatment of moderate to severe Alzheimer's disease, use is made of NMDA receptor antagonists.

The development of Alzheimer's disease is caused by neurodegenerative processes with cell loss in the cortex or regions of the brain. Cholinergic nerves, including the areas innervated thereby, are especially affected. In the early stage of the disease, the glutamatergic system is disrupted. As a result of an excessive calcium influx into the neurones, in the long term neurodegeneration can occur. As the most important glutamatergic synapse, the NMDA complex has a central role to play here. Inhibition of the complex by means of a selective antagonist can protect the neuronal areas from excitatory damage.

Signs of Alzheimer's disease are strongly enlarged ventricles, microscopically detectable plaques, and neurofibrillary tangles. The clinical picture is usually characterized by memory loss and by a gradual decline in personality and intellect. In this respect, the goal of an Alzheimer's treatment is to alleviate personal suffering and thus to counteract social isolation. A curative therapy is currently not available. In this respect, it is desirable to delay appropriately the development of the dementia, which usually proceeds progressively. A palliative therapy has the following goals: improvement of cognitive function, minimization of noticeable neurological behavioral patterns, delaying of the progression of the disease, and prevention of seizure symptoms.

According to the prior art, it is known that NMDA receptor antagonists are suitable as neuroprotectors, by preventing the damaging effect of glutamate at NMDA receptors. The group of the NMDA receptor antagonists include, for example, substances such as MK 801, dextromethorphan, ketamine, memantine, amantadine, dextrorphan, felbamate, acamprosate, MRZ 2/579, phencyclidine, aptiganel, and these are a possibility both as individual substances and as mixtures or as physiologically compatible salts thereof, for example hydrochlorides, citrates, maleates, etc.

It is known that the use of NMDA receptor antagonists is limited especially as a result of psychomimetic secondary effects; in this respect, the widespread use thereof has not been seen to date. Especially important in the treatment of Alzheimer's patients is the NMDA receptor antagonist memantine (3,5-dimethyl-9-aminoadamantane) or the hydrochloride thereof. Memantine is approved for the treatment of moderate to severe Alzheimer's disease. The medication is available in Germany under the name Axura®. The drug is available in the form of oral drops for ingestion or as film-coated tablets. The administration of the medication must be carried out only under the supervision of a carer, and the dose of active ingredient has to be increased stepwise over a period of several weeks in order to minimize in particular the secondary effects described for the treatment of moderate to severe Alzheimer's disease, such as, inter alia, hallucinations, disorientation, dizziness, headaches, and fatigue. After the starting phase, the medication must also be strictly administered once in the morning and once in the afternoon (drops) or, when using the film-coated tablets, at the same time every day.

This strict therapy schedule and the associated need for supervision result in the disadvantageous situation of a very high degree of effort or high therapy costs for the care of these patients.

Owing to the abovementioned disadvantages, there is a need for novel therapeutic systems which overcome these disadvantages, more particularly such systems in which the degree of effort for patient care can be reduced.

According to the prior art, it is known that NMDA receptor antagonists can optionally be used in combination with analgesics in topical dosage forms for the treatment of local pain (WO 00/03716 whose United States equivalent is U.S. Pat. No. 7,700,122; WO 03/015 699 whose United States equivalent is United States Publication No. US 2003082214A1 and US 2004076648A1; US 2002/0016319, U.S. Pat. No. 6,194,000). US 2004/0102525, US 2003/0139698, and WO 04/009062 (whose United States equivalent is United States Publication No. US 2004019118A1 and US 2009005459A1); also disclose the administration of NMDA receptor antagonists. WO 04/106275 (whose United States equivalent is United States Publication No. US 2007010507A1 and US 2007048385A1), discloses specific salts of NMDA receptor antagonists.

However, the dosage forms of the prior art are not suitable, or only suitable to a limited extent, for establishing, after topical administration, systemic plasma concentrations of NMDA receptor antagonists which achieve a sufficient pharmacological effect for a sufficient duration. With respect to transcutaneous permeability, no experimental data are disclosed in the prior art.

However, in the prevention or treatment of diseases of the central nervous system, it would be especially desirable to have specifically dosage forms which can maintain pharmacologically effective plasma concentrations over a comparatively long period (e.g., 12 h, 24 h, or longer), not least because, in such cases, the degree of effort for care personnel to care for patients might be reduced.

SUMMARY OF ADVANTAGEOUS EMBODIMENTS OF THE INVENTION

Therefore, the object of the invention is to provide a dosage form for the treatment or prevention of diseases of the central nervous system, more particularly dementias, preferably Alzheimer's disease, which has advantages over the dosage forms of the prior art.

The advantages can be expressed in terms of usability, dosage, and/or compatibility. As far as possible, the dosage form should ensure in a one-off administration pharmacologically effective plasma concentrations of the active ingredient over a prolonged period, for example for at least 12 h, preferably for at least 24 h, or even for a number of days, so that renewed administration and thus also renewed monitoring by the care personnel are required less often (e.g., only once a day).

This object is achieved by the subject matter of the claims.

DETAILED DESCRIPTION OF ADVANTAGEOUS EMBODIMENTS OF THE INVENTION

It was found that, surprisingly, a Transdermal Therapeutic System can be produced which is suitable for administering memantine transdermally, it being possible to achieve the administration for at least 12 h for example or, for example, over a prolonged period, for at least 24 h for example, and during this period pharmacologically effective plasma concentrations of memantine can be maintained.

The invention provides a Transdermal Therapeutic System (TTS) for administering the active ingredient memantine in the form of the free base or of a physiologically compatible salt or prodrug, wherein the TTS has
- a backing impermeable to active ingredient;
- at least one active-ingredient-containing layer which comprises a storage material into which the active ingredient is introduced;
- optionally a release liner;
- a $t_{max}$ of at least 24 h;

and wherein consecutive or staggered, preferably repeated, administration of one or more of the Transdermal Therapeutic Systems at a time for administration intervals each lasting at least 12 h independently of one another, preferably over a total period of at least 300 h, achieves, in the blood plasma of the individual requiring treatment, the following active ingredient concentrations from the beginning in each case of the first administration:
- after 24 h, at least 14 ng/ml, preferably at least 16.2 ng/ml,
- after 48 h, at least 27 ng/ml, preferably at least 29.2 ng/ml,
- after 60 h, at least 32 ng/ml, preferably at least 34.5 ng/ml,
- after 72 h, at least 37 ng/ml, preferably at least 39.1 ng/ml,
- after 96 h, at least 44 ng/ml, preferably at least 46.6 ng/ml,
- after 144 h, at least 54 ng/ml, preferably at least 56.5 ng/ml,
- after 192 h, least 60 ng/ml, preferably at least 62.3 ng/ml,
- after 240 h, at least 63 ng/ml, preferably at least 65.5 ng/ml and
- after 300 h, at least 65 ng/ml, preferably at least 7.8 ng/ml.

Preferably, the maximum release rate of the active ingredient is no more than 100 μg/cm³.

The TTS according to the invention comprises the active ingredient memantine (3,5-dimethyladamantane-1-amine) in the form of the free base or of a physiologically compatible salt or prodrug. For the purposes of the description, the term "active ingredient" comprises memantine and physiologically compatible solvates thereof. Memantine can be present in the form of the free base, in the form of the physiologically compatible salts and/or in the form of the solvates, more particularly the hydrates, or optionally in the form of any mixtures of the aforementioned compounds.

In a preferred embodiment, the TTS according to the invention comprises memantine in the form of the free base. The fundamental preparation of a free base from a hydrochloride is known to a person skilled in the art. For example, this can be achieved using ion exchangers. A further method is extraction from an alkaline aqueous environment using organic solvents which are usually immiscible with water or only slightly miscible. The free base (3,5-dimethyladamantane-1-amine) is obtained by removing the organic solvent.

In another preferred embodiment, the TTS according to the invention comprises memantine in the form of a physiologically compatible salt. Preferred physiologically compatible salts of memantine are, for example, the hydrochloride, hydrobromide, sulfate, hydrogen sulfate, phosphate, hydrogen phosphate, dihydrogen phosphate, acetate, propionate, lactate, citrate, ascorbate, formate, fumarate, maleate, sebacate, mesylate, and besylate thereof. Particular preference is given to memantine hydrochloride.

The TTS according to the invention can comprise prodrugs of memantine. Prodrug in this context means an inactive or less active pharmacological substance which is converted to an active ingredient (metabolite) only as a result of metabolism in the organism. Examples of prodrugs of memantine or the physiologically compatible salts thereof are derivatized at the amino function, for example amidated with physiologically compatible carboxylic acids. These amides are then cleaved under physiological conditions, by enzyme catalysis if applicable. Another example of a prodrug of memantine is the N-oxide thereof.

The TTS according to the invention can comprise further pharmacologically active substances as active ingredient besides memantine or physiologically compatible salts thereof or prodrugs. However, preferably no further active ingredients are present besides memantine or physiologically compatible salts thereof.

Preferably, the TTS according to the invention is an active-ingredient-containing plaster.

Usually, such a TTS comprises at the least
a) one backing layer impermeable to active ingredient; preference is given to a backing layer which is impermeable to water in liquid form and/or water vapor;
b) at least one active-ingredient-containing layer which at least partly covers the backing layer and is preferably itself equipped to be pressure-sensitively adhesive. Optionally, an additional pressure-sensitively adhering layer can be applied in order to ensure sufficient adhesion on the skin;
c) optionally a release liner which covers the active-ingredient-containing layer and can be peeled off therefrom. Preference is given to a release liner which is impermeable to water in liquid form and/or water vapor.

The optional release liner is usually removed before the administration of the TTS in order to expose the adhesive layer. The release liner can, for example, consist of polyethylene, polyester, polyethylene terephthalate, polypropylene, polysiloxane, polyvinyl chloride or polyurethane and, optionally, of treated paper fibers, such as cellophane for example, and can optionally have a silicone, fluorosilicone or fluorocarbon coating.

The TTS according to the invention has a backing layer impermeable to active ingredient and one or more active-ingredient-containing layers, but not all layers besides the backing layer have to contain active ingredient.

In a preferred embodiment, the TTS according to the invention has in total no more than 3, 4, 5, 6, 7, 8 or 9 different layers. In another preferred embodiment, the TTS according to the invention has in total at least 3, 4, 5, 6, 7, 8 or 9 different layers.

The backing layer impermeable to active ingredient (surface layer) of the TTS according to the invention is preferably impermeable to the substances present in the active-ingredient-containing layer and in the adhesive layer, more particularly to the active ingredient possibly present, and is preferably inert and can be formed from polymers such as polyesters, for example polyethylene phthalate, polyolefins, such as polyethylenes, polypropylenes or polybutylenes, polycarbonates, polyethylene oxides, polyterephthalates such as polyethylene terephthalates, polyurethanes, polystyrenes, polyamides, polyimides, polyvinyl acetates, polyvinyl chlorides and/or polyvinylidene chlorides, copolymers such as acrylonitrile/butadiene/styrene copolymers containing paper fibers, textile fibers and/or mixtures thereof, which can be metallized or pigmented if required. The backing layer can also be formed from a combination of metal foil and polymeric layer. The polymers specified can be used as film, fabric, felt, or foam.

The layer impermeable to active ingredient preferably has a layer thickness in the range from 15 to 2000 µm.

The TTS according to the invention has an active-ingredient-containing layer which comprises a storage material into which the active ingredient is introduced. This active-ingredient-containing layer can in addition be pressure-sensitively adhesive, by the active ingredient being present dissolved and/or dispersed in a matrix together with the adhesive (drug in adhesive). However, the active-ingredient-containing layer and adhesive layer can also be separate in the TTS according to the invention.

The active-ingredient-containing layer preferably has a layer thickness in the range from 10 to 9000 µm.

The TTS according to the invention can, for example, be in the form of a membrane-controlled system (reservoir TTS) or a diffusion-controlled system (matrix TTS) (cf. K. H. Bauer, et al., Pharmazeutische Technologie [Pharmaceutical Technology]; R. H. Müller, et al., Pharmazeutische Technologie: Moderne Arzneiformen [Pharmaceutical Technology: Modern Dosage Forms]).

A reservoir TTS usually comprises a flat pouch which is self-adhesive on the skin and comprises the active ingredients in dissolved form. Facing the skin side, the pouch is equipped with a membrane which is permeable to the active ingredient and controls the release of active ingredient. The adhesive layer and active-ingredient-containing layer (reservoir) are usually spatially separated subunits.

In the case of a matrix TTS, the active ingredient is embedded in a matrix and can be present in dissolved form or dispersed in a liquid, semi-solid or solid state. If the matrix has in addition adhesive properties, the adhesive layer is also in addition the active-ingredient-containing layer (drug in adhesive). However, it is also possible for the adhesive layer and the active-ingredient-containing layer— as for a reservoir TTS—to be separate. In this case, the adhesive layer can be applied completely, partially or annularly on the active-ingredient-containing layer or on the membrane of the reservoir.

The composition and structuring of the matrix and/or of the membrane make it possible to regulate the release of the active ingredient. With regard to further details, reference can be made to, for example, T. K. Ghosh, Transdermal and Topical Drug Delivery Systems, CRC Press, 1997; R. O. Potts et al., Mechanisms of Transdermal Drug Delivery (Drugs and the Pharmaceutical Sciences), Marcel Dekker, 1997; and R. Gurny et al., Dermal and Transdermal Drug Delivery. New Insights and Perspectives, Wissenschaftliche VG., Stuttgart, 1998.

Adhesives which can be used to produce the adhesive layer of the TTS according to the invention are pressure-sensitive adhesives (PSAs). The adhesive layer can, for example, be formed as an adhesive region or adhesive surface which borders the active-ingredient-containing layer laterally. Suitable for producing the adhesive layer are, for example, polymers such as polyacrylates, polyvinyl ethers, polyisobutylenes (PIBs), styrene/isoprene or butadiene/styrene copolymers or polyisoprene rubbers. Also suitable are silicone adhesives, such as optionally crosslinked polydimethylsiloxanes, for example. Moreover, resins such as, for example, esters of glycines, glycerol or pentaerythritol, or hydrocarbon resins such as polyterpenes, are suitable. Adhesives based on acrylates are produced by polymerization of acrylates, methacrylates, alkyl acrylates and/or alkyl methacrylates, optionally with further unsaturated monomers, such as acrylamide, dimethylacrylamide, dimethylaminoethyl acrylate, hydroxyethyl acrylate, hydroxypropyl acrylate, methoxyethyl acrylate, methoxyethyl methacrylate, acrylonitrile and/or vinyl acetate. Examples of suitable polymers are available commercially under the name Durotak®, for example the products 2516, 2287, 900A or 9301. Other suitable commercially available polymers are polyisobutylenes, polyacrylates such as, for example, GMS 3083, Plastoid B and Eudragit® E 100.

The adhesive layer can additionally comprise excipients, such as plasticizers, for example phthalates such as dibutyl phthalates, mineral oils, esters of citric acid, or esters of glycerol, skin penetration enhancers, for example dimethyl sulfoxide, tackifiers, fillers (such as zinc oxide or silica), crosslinkers, preservatives and/or solvents. Such excipients are known to a person skilled in the art. In this regard, reference can be made to, for example, R. Niedner et al., Dermatika: therapeutischer Einsatz, Pharmakologie und Pharmazie [Dermatics: Therapeutic Use, Pharmacology and Pharmacy], Wiss. Verl.-Ges. 1992; H. P. Fiedler, Lexikon der Hilfsstoffe für Pharmazie, Kosmetik und angrenzende Gebiete [Encyclopedia of Excipients for Pharmacy, Cosmetics and Related Fields], Editio Cantor Aulendorf, 2002.

The active ingredient is present in the active-ingredient-containing layer in dissolved or solid form. Preferably, the active ingredient is present in completely dissolved form, i.e., preferably practically no crystalline portions of the active ingredient can be detected. In a preferred embodiment, the concentration of the active ingredient in the active-ingredient-containing layer according to the invention is at least 25%, more preferably at least 50%, even more preferably at least 66%, most preferably at least 75%, and in particular, however, at least 80%, of its saturation concentration. A person skilled in the art knows how to determine the saturation concentration. For example, the saturation concentration has yet to be reached when a crystal of the pure active ingredient is contacted with the active-ingredient-containing layer and is absorbed, i.e., dissolved, thereby within 5 minutes. If the active ingredient is present at least partially in solid form, the system is preferably a microdispersion.

The active-ingredient-containing layer of the TTS according to the invention comprises a storage material into which the active ingredient is introduced.

In a preferred embodiment, the storage material is arranged between the active-ingredient-impermeable backing layer and an active-ingredient-permeable membrane material, and so the TTS according to the invention is preferably a reservoir TTS.

In another preferred embodiment, the storage material serves as a matrix, and so the TTS according to the invention is preferably a matrix TTS.

Suitable storage materials are natural or (semi)synthetic matrix-forming polymers. Matrix-forming polymers which may be mentioned are, for example, polyethylenes, chlorinated polyethylenes, polypropylenes, polyurethanes, polycarbonates, polyacrylic esters, polyacrylates, polymethacrylates, polyvinyl alcohols, polyvinyl chlorides, polyvinylidene chlorides, polyvinyl-pyrrolidones, polyethylene terephthalates, polytetrafluoroethylenes, ethylene/propylene copolymers, ethylene/ethyl acrylate copolymers, ethylene/vinyl acetate copolymers, ethylene/vinyl alcohol copolymers, ethylene/vinyl-oxyethanol copolymers, vinyl chloride/vinyl acetate copolymers, vinyl-pyrrolidone/ethylene/vinyl acetate copolymers, rubbers, rubber-like synthetic homopolymers, copolymers or block polymers, silicones, silicone derivatives such as polysiloxane/polymethacrylate copolymers, cellulose derivatives, such as cellulose ethers, more particularly methylcellulose, ethylcellulose, propylcellulose, hydroxyethylcellulose, hydroxypropylcellulose, hydroxypropylmethylcellulose, carboxymethylcellulose and/or mixtures thereof. Particular preference is given to polyacrylates or polysilicones.

The storage material can comprise the abovementioned polymers which are suitable for producing the adhesive layer (drug in adhesive).

The amount of storage material is preferably from 10 to 99.9% by weight based on the total weight of the active-ingredient-containing layer, more preferably from 50 to 95% by weight.

With regard to the proportions of storage material to active ingredient content, preference is given to selecting ratios of from 99:1 to 50:50 (mass of storage material:mass of active ingredient), preferably from 95:5 to 60:40. In preferred embodiments, the selection is from 99.5:0.5 to 80:20 (mass of matrix:mass of active ingredient), preferably from 99:1 to 85:15. The reason for the relatively high proportion of active ingredient is the relatively high level of substance needed for treating moderate to severe Alzheimer's disease.

Preferably, the storage material comprises
a preparation which is in liquid or gel form and in which the active ingredient is partly or completely dissolved; and/or
a matrix which is based on a polymeric material and in which the active ingredient is dissolved or distributed as a microdispersion; and/or
a polyacrylate- or polysilicone-based polymeric material; and/or
a lipogel which preferably contains from 10 to 50% by weight of active ingredient.

In a preferred embodiment, the active-ingredient-containing layer comprises a hydrogel or a lipogel. For the purposes of the description, hydrogels are gels which comprise water and/or other substances which are hydrophilic or completely or partially miscible with water, said substances giving the gel its hydrophilic properties. For the purposes of the description, lipogels are gels which mainly comprise substances which are not miscible with water and which give the gel its lipophilic properties.

In a preferred embodiment, the active ingredient is present in the active-ingredient-containing layer as a physiologically compatible salt, more particularly as memantine hydrochloride. Preferably, the active-ingredient-containing layer additionally comprises at least one basic material, the basicity of which is sufficient to react with the physiologically compatible salt of the active ingredient to release the free base of the active ingredient. Suitable basic materials are known to a person skilled in the art and their suitability can be assessed on the basis of the $pK_a$ value of the memantine base. Preferably, the basic material is selected from the group consisting of polymers having basic side groups, organic bases and inorganic bases. In a preferred embodiment, the basic material is selected from the group consisting of acrylate-based polymers which have aminoalkyl side groups; inorganic oxides or hydroxides, more particularly alkali metal oxides or alkaline earth metal oxides; organic amines or salts thereof; alkali metal alcoholates or carboxylates or alkaline earth metal alcoholates or carboxylates.

Preferred examples of suitable basic materials are calcium oxide (CaO), sodium ethanolate, and basic methacrylate copolymers such as, for example, Eudragit® E 100.

In a preferred embodiment, the active-ingredient-containing layer comprises from 20 to 90% by weight of storage material, from 10 to 50% by weight of active ingredient, and optionally from 5 to 40% by weight of basic material, based on the total weight of the active-ingredient-containing layer.

The active-ingredient-containing layer of the TTS according to the invention can comprise not only the active ingredient and the adhesive possibly present but also tackifiers, plasticizers, permeation promoters, viscosity-enhancing substances, solubilizers, crosslinkers, preservatives, emulsifiers, thickeners and/or other customary excipients. Such additives are known to a person skilled in the art.

Examples of solubility-enhancing agents and/or permeation promoters are acetylacetone, acetyl tributyl citrate, acetyl triethyl citrate, benzyl alcohol, butyl stearate, cetyl lactate, cetyl palmitate, cetyl stearate, cetylstearyl alcohol/cetyl alcohol, chlorobutanol, cineol, decyl methyl sulfoxide, decyl oleate, dibutyl phthalate, diethylene glycol monoethyl ether, diethyl phthalate, diethyl sebacate, diisopropyl adipate, dimethyl phthalate, dioctyl adipate, dipropylene glycol, glyceryl monooleate, glyceryl monostearate, stearyl alcohol, peanut oil, ethyl lactate, ethyl linoleate, ethyl (9,12,15)-linolenate, eugenol, farnesol, glycerol, glyceryl acetyl ester, glyceryl stearate, glycol distearate, glyoxal, hexadecanol, hexylene glycol, isobutyl stearate, isocetyl stearate, isodecyl oleate, isopropyl lanolate, isopropyl myristate/isopropyl palmitate, isopropyl stearate, isostearyl neopentanoate, lauric acid diethanolamide, limonene, linolenic acid, linolenic acid diethanolamide, mint camphor, myristyl lactate, myristyl myristate, myristyl stearate, m-tolyl acetate, octyldodecanol, octyl palmitate, octyl stearate, oleic acid diethanolamide, oleyl alcohol, oleyl oleate, phenylethyl alcohol, propylene glycol, propylene carbonate, isostearic acid, octanoic acid, hydrogenated castor oil, 1,3-butylene glycol, safflower oil, squalane, squalene, triacetin, glyceryl triacetate, triethyl citrate, undecylenic acid, (+)-fenchone, ammonium lauryl ether sulfate, cholesterol, lecithin, glycerol hydroxystearate, mono- and diglycerides of fatty acids, sodium caprylate, sodium lauryl ether sulfate, Na/K salts of fatty acids, Na lauryl sulfate, PEG-2 stearate, sodium sulfosuccinate, polyglyceryl esters of fatty acids, polyoxyethylene alkyl ethers, cetomacrogol, polyoxyethylene fatty acid sorbitan esters, propylene glycol stearate, sorbitan fatty acid esters, stearic acid diethanolamide, medium-chain (preferably $C_{12}$-$C_{14}$) triglycerides (according to Ph. Eur.).

Solubilizers which can be used are N-methyl-2-pyrrolidone, laurylpyrrolidone, triethanolamine, triacetin, diethylene glycol monoethyl ether, derivatives of fatty acids or fatty alcohols and/or low molecular weight polyhydric alcohols such as, for example, propylene glycol or glycerol.

For the purposes of the description, a viscosity-enhancing substance is preferably a gel former, i.e., a substance which, firstly, enhances the viscosity of the composition and, secondly, supports the gel formation thereof. Examples of such viscosity-enhancing substances are gelatins (e.g., gelatin), carob flour (e.g., CESAGUM® LA-200, CESAGUM® LID/150, CESAGUM® LN-1), pectins such as citrus pectin (e.g., CESAPECTIN® HM Medium Rapid Set), apple pectin, pectin from lemon peel, waxy maize starch (C*GEL® 04201), sodium alginate (e.g., FRIMULSION® ALG (E401)), guar gum (e.g., FRIMULSION® BM, POLYGUM® 26/1-75), iota-carrageenan (e.g., FRIMULSION® D021), karaya gum, gellan gum (e.g., KELCOGEL® F, KELCOGEL® LT100), galactomannan (e.g., MEYPROGAT® 150), tara gum (e.g., POLYGUM® 43/1), propylene glycol alginate (e.g., PROTANAL® Ester SD-LB), sodium hyaluronate, tragacanth, tara gum (e.g., VIDOGUM® SP 200), fermented polysaccharide Welan Gum (e.g., K1A96), xanthan gum (e.g., XANTURAL® 180).

When the TTS according to the invention is formed according to the reservoir system, the reservoir membrane can consist of inert polymers, such as, for example, polyethylenes, polypropylenes, polyvinyl acetates, polyamides, ethylene/vinyl acetate copolymers and/or silicones. The reservoir membrane makes it possible to achieve a controlled release of the active ingredient from the reservoir.

The active-ingredient-containing matrix or the active-ingredient-containing reservoir can also comprise a solvent, such as, for example, water, ethanol, 1-propanol, isopropanol, low molecular weight polyhydric alcohol, for example propylene glycol or glycerol, or an ester, such as isopropyl myristate, or mixtures thereof. In a preferred embodiment, the active-ingredient-containing matrix or the active-ingredient-containing reservoir contains, however, substantially no ethanol and/or no isopropanol.

Preservatives for the active-ingredient-containing layer which can be used are antioxidants, such as vitamin E, butylated hydroxytoluene, butylated hydroxyanisole, parabens, ascorbic acid, ascorbyl palmitate, and/or chelating agents, such as disodium ethylenediamine-tetraacetic acid, potassium or sodium citrate. Moreover, suitable preservatives are PHB esters, such as PHB methyl ester and PHB propyl ester, benzalkonium chloride, chlorhexidine, sorbic acid, benzoic acid, propionic acid, salicylic acid and salts thereof, formaldehyde and paraformaldehyde, hexachlorophene, o-phenylphenol, zinc pyrithione, inorganic sulfites, sodium iodate, chlorbutol, dehydroacetic acid, formic acid, dibromohexamidine, merthiolate, phenylmercuric salts (phenyl-Hg compounds), undecylenic acid, hexetidine, bronidox, bronopol, 2,4-dichlorobenzyl alcohol, triclocarban, parachlorometacresol, triclosan, parachlorometaxylenol, imidazolidinylurea derivatives, polyhexamethylene biguanide hydrochloride, phenoxyethanol, methenamine, Dowicil 200, 1-imidazolyl-(4-chlorophenoxy)-3,3'-dimethylbutan-2-one, dimethylhydantoin, benzyl alcohol, 1-hydroxy-4-methyl-6-(2,4,4-trimethylpentyl)-2-pyridone, 1,2-dibromo-2,4-dicyanobutane, 3,3'-dibromo-5,5'-dichloro-2,2-dihydroxydiphenylmethane, isopropyl-metacresol, and Kathon.

The TTS according to the invention can also comprise, in one or more layers, at least one plasticizer selected from the group encompassing long-chain alcohols such as dodecanol, undecanol, octanol, esters of carboxylic acids with polyethoxylated alcohols, diesters of aliphatic dicarboxylic acids such as adipic acid, and medium-chain triglycerides of caprylic acid and/or capric acid, coconut oil, polyhydric alcohols such as 1,2-propanediol, esters of polyhydric alcohols such as glycerol with levulinic acid or caprylic acid, and etherified polyhydric alcohols.

The TTS according to the invention can be produced according to the known production processes, more particularly for active-ingredient-containing patches with process steps such as lamination, punching, delamination, unwinding, cutting, rewinding, mounting or metering (cf. Verpackungs-Rundschau 4/2002, 83-84).

The active ingredient is released from the TTS according to the invention preferably in a controlled manner. The TTS according to the invention preferably has a maximum active ingredient release rate of not more than 100 µg/cm$^2$ per h, preferably not more than 95 µg/cm$^2$ per h, not more than 90 µg/cm$^2$ per h or not more than 85 µg/cm$^2$ per h; more preferably not more than 80 µg/cm$^2$ per h, not more than 75 µg/cm$^2$ per h or not more than 70 µg/cm$^2$ per h; even more preferably not more than 65 µg/cm$^2$ per h, not more than 60 µg/cm$^2$ per h or not more than 55 µg/cm$^2$ per h; most preferably not more than 50 µg/cm$^2$ per h, not more than 45 µg/cm$^2$ per h or not more than 40 µg/cm$^2$ per h; and in particular not more than 35 µg/cm$^2$ per h or not more than 32 µg/cm$^2$ per h.

In a preferred embodiment, the maximum active ingredient release rate is in the range of 20±15 µg/cm$^2$ per h, more preferably 20±12.5 µg/cm$^2$ per h, even more preferably 20±10 µg/cm$^2$ per h, most preferably 20±7.5 µg/cm$^2$ per h, and in particular 20±5 µg/cm$^2$ per h. In another preferred embodiment, the maximum active ingredient release rate is in the range of 25±10 µg/cm$^2$ per h, even more preferably 25±7.5 µg/cm$^2$ per h, most preferably 25±5 µg/cm$^2$ per h, and in particular 25±2.5 µg/cm$^2$ per h. In another preferred embodiment, the maximum active ingredient release rate is in the range of 30±5 µg/cm$^2$ per h, even more preferably 30±2.5 µg/cm$^2$ per h.

Usually, the release rate changes during the administration interval of the TTS. For instance, the amount of active ingredient in the TTS continuously decreases as a result of the release, and also the skin can develop a certain storage effect. Both effects can influence the release rate.

The maximum release rate of a TTS and determination thereof are known to a person skilled in the art. The maximum release rate can be specified as the maximum permeation of human skin and determined in vitro using, for example, a Franz cell. Preferably, it is determined under the conditions set out in the experimental part.

The TTS according to the invention has a $t_{max}$ of at least 24 h, more preferably at least 26 h, even more preferably at least 28 h, most preferably at least 30 h, and in particular at least 32 h. In a preferred embodiment of the TTS according to the invention, $t_{max}$ is in the range of 36±12 h, more preferably 36±10 h, even more preferably 36±8 h, most preferably 36±6 h, and in particular 36±4 h. In another preferred embodiment of the TTS according to the invention, $t_{max}$ is in the range of 32±8 h, more preferably 32±7 h, even more preferably 32±6 h, most preferably 32±5 h, and in particular 32±4 h. In a further preferred embodiment of the TTS according to the invention, $t_{max}$ is in the range of 28±4 h, more preferably 28±3 h, most preferably 28±2 h.

Preferably, $t_{max}$ is defined as the time which has elapsed before the maximum active ingredient concentration in the blood plasma ($C_{max}$) is reached during the one-off and first administration of the TTS according to the invention, measured starting from the application of the TTS on the skin. Suitable methods for determining $t_{max}$ and $C_{max}$ are known to a person skilled in the art.

The TTS according to the invention preferably has a $C_{max}$ of at least 4 ng/ml, at least 4.5 ng/ml, at least 5 ng/ml, or at least 5.5 ng/ml, more preferably at least 6 ng/ml, even more preferably at least 8 ng/ml, most preferably at least 10 ng/ml, and in particular at least 12 ng/ml.

The TTS according to the invention preferably has a pharmacokinetic delay $t_{lag}$ of not more than 6 h, more preferably 1.33±1.00 h, even more preferably 1.33±0.66 h, and in particular 1.33±0.33 h. The pharmacokinetic delay $t_{lag}$ of the TTS according to the invention is thus surprisingly short, and this is advantageous. For instance, effective plasma concentrations of the active ingredient are reached in a comparatively short time after the application of the TTS on the skin.

The TTS according to the invention preferably has duration of bioanalytical detectability $t_{last}$ of at least 200 h, more preferably at least 220 h, and in particular at least 240 h.

The TTS according to the invention preferably has a pharmacokinetic active ingredient half-life $t_{1/2,z}$ in the range of 60-100 h, more preferably in the range of 52±25 h, more preferably 52±15 h, most preferably 52±10 h, and in particular 52±5 h.

Suitable methods for determining these pharmacokinetic parameters are known to a person skilled in the art. Determining the active ingredient concentration in the blood plasma is likewise known to a person skilled in the art. It is preferably carried out by LC, for example HPLC, preferably coupled to MS (LC-MS or HPLC-MS).

The TTS according to the invention preferably has a low interindividual variability, preferably not more than 25%, more preferably not more than 20%. The advantage of such a low interindividual variability is that the blood levels reached in vivo can be accurately predicted, and this is also associated with, inter alia, increased therapeutic safety.

With an interindividual variability of the pharmacokinetic parameters of not more than 25%, the TTS according to the invention differs from other TTSs which are intended for administering other active ingredients. For example, a TTS for administering the active ingredient rivastigmine has been reported, for which the variability of the parameters is >32% (cf. G. Lefèvre et al., Clinical Pharmacology & Therapeutics, 83(1), 2008, 106-114).

In a preferred embodiment, the TTS according to the invention has, after its intended use, a comparatively low residual content of active ingredient. Preferably, the residual content after administration for 24 h is not more than 75% by weight, more preferably not more than 70% by weight, even more preferably not more than 65% by weight, and in particular not more than 60% by weight, of the amount originally present in the TTS. For reasons of economy and also safety, this is advantageous.

The TTS according to the invention is formed such that consecutive, or staggered, preferably repeated, administration of one or more of the TTSs according to the invention at a time for administration intervals each lasting at least 12 h independently of one another over a total period of at least 300 h achieves, in the blood plasma of the individual requiring treatment, the following active ingredient concentrations from the beginning in each case of the first administration:

after 24 h, at least 14 ng/ml, preferably at least 16.2 ng/ml,
after 48 h, at least 27 ng/ml, preferably at least 29.2 ng/ml,
after 60 h, at least 32 ng/ml, preferably at least 34.5 ng/ml,
after 72 h, at least 37 ng/ml, preferably at least 39.1 ng/ml,
after 96 h, at least 44 ng/ml, preferably at least 46.6 ng/ml,
after 144 h, at least 54 ng/ml, preferably at least 56.5 ng/ml,
after 192 h, at least 60 ng/ml, preferably at least 62.3 ng/ml,
after 240 h, at least 63 ng/ml, preferably at least 65.5 ng/ml, and
after 300 h, at least 65 ng/ml, preferably at least 67.8 ng/ml.

The repeated administration is preferably carried out consecutively without delays, i.e., when the one or more TTSs according to the invention are removed at the end of an application interval, the one or more TTSs according to the invention for the following application interval are applied immediately. Preferably, the time interval at which there may be no TTSs according to the invention at all applied to the body is no more than 10 minutes, more preferably no more than 5 minutes.

In a preferred embodiment, all TTSs according to the invention are administered on the same skin area of the individual over the total period, i.e., a given skin area of the individual is overlaid or plastered repeatedly with TTSs according to the invention.

In another preferred embodiment, all TTSs according to the invention are administered each time on different skin areas of the individual over the total period, i.e., a given skin area of the individual is not overlaid or plastered repeatedly with TTSs according to the invention.

The TTSs according to the invention are applied for consecutive administration intervals each lasting at least 12 h independently of one another, preferably over a total period of at least 300 h. When each administration interval lasts, for example, 12 h, then at least 25 consecutive administration intervals are required in order to cover the total period of at least 300 h. When each administration interval lasts, for example, 18 h, then, accordingly, at least 17 consecutive administration intervals are required in order to cover the total period of at least 300 h.

The individual administration intervals can have the same length or differ in length. Preferably, all administration intervals are equally long, preferably 12 h, 14 h, 16 h, 18 h, 20 h, 22 h, 24 h, 26 h, 28 h, 30 h, 32 h, 34 h, 36 h, 38 h, 40 h, 42 h, 44 h, 46 h, 48 h, 50 h, 52 h, 54 h, 56 h, 58 h, 60 h, 62 h, 64 h, 66 h, 68 h, 70 h or 72 h each. In a preferred embodiment, each administration interval is, independently of the others, not more than 168 h or not more than 144 h, more preferably not more than 120 h or not more than 96 h, even more preferably not more than 72 h or not more than 48 h, more preferably not more than 36 h or not more than 24 h, and in particular not more than 12 h.

Figure 1:
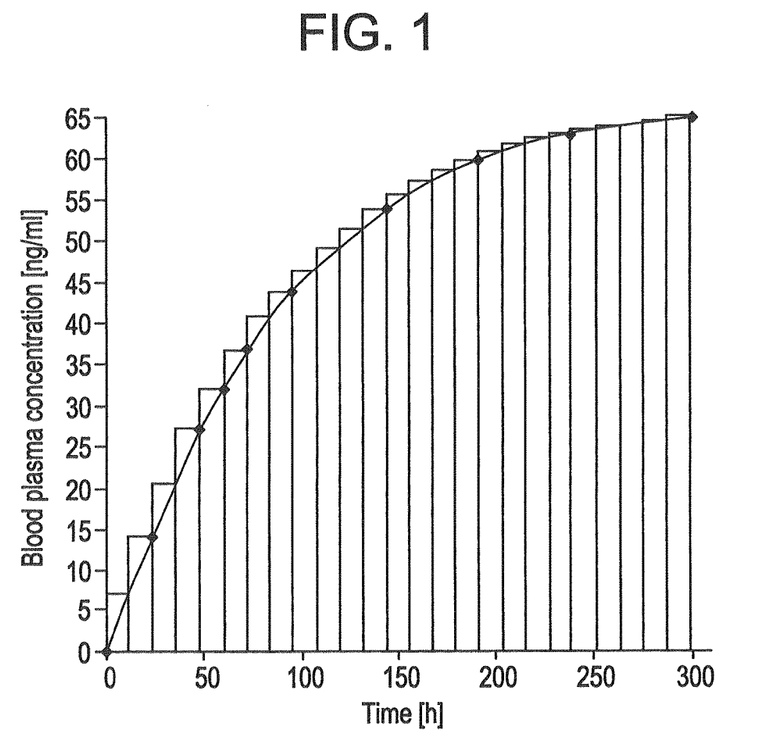
FIGS. 1 and 2 schematically illustrate an exemplary course of the minimum blood plasma concentration of the active ingredient over time.
Figure 2:
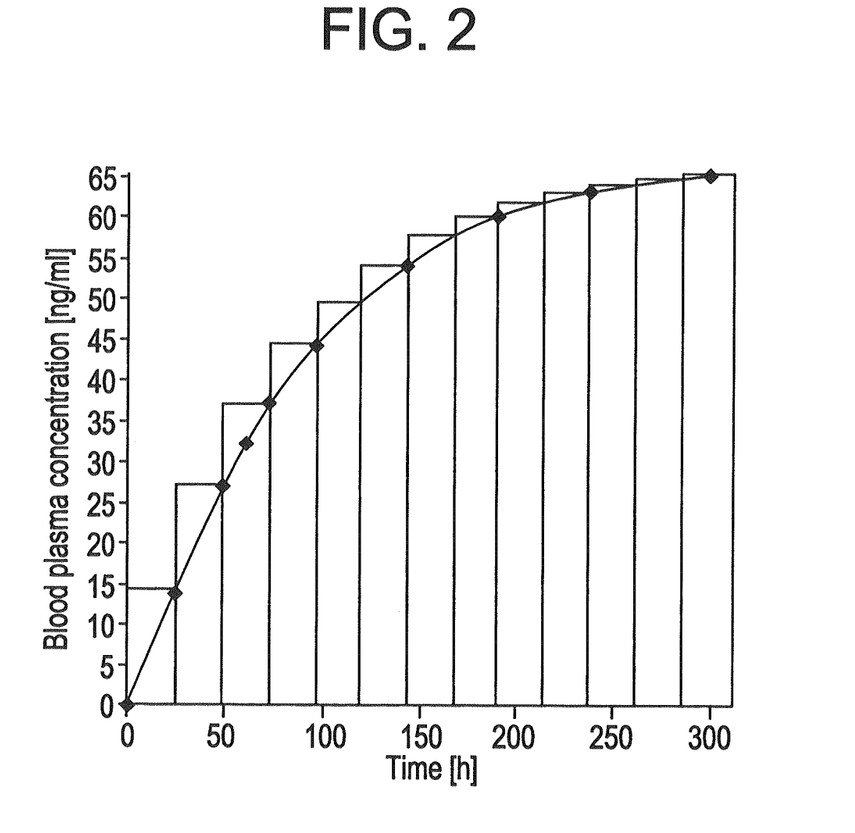

The administration intervals are explained in more detail in FIGS. 1 and 2. Both figures show schematically the course of the minimum blood plasma concentration of the active ingredient over time. In FIG. 1, each bar in the chart represents an administration interval of 12 h; in FIG. 2, each bar represents an administration interval of 24 h. The height of the bars represents in each case the minimum blood plasma concentration attained.

During each administration interval, it is possible to apply a single TTS according to the invention or to apply, simultaneously in each case, multiple TTSs according to the invention. The number of the TTSs applied can differ from administration interval to administration interval. Preferably, the number of the TTSs applied is identical in each administration interval.

In a preferred embodiment, the active ingredient concentrations mentioned are achieved upon administering one TTS according to the invention per administration interval or upon administering, simultaneously, two, three, four, five, six, seven, eight, nine, ten, eleven, twelve, thirteen, fourteen, fifteen or sixteen TTSs according to the invention per administration interval.

In a preferred embodiment, for each administration interval, the duration in h divided by the number of the, if applicable, simultaneously applied TTSs is independently in the range from 4 to 24, more preferably from 5 to 20, even more preferably from 6 to 18. In a preferred embodiment, for each administration interval, the duration in h divided by the number of the, if applicable, simultaneously applied TTSs is independently in the range from 3 to 8, more preferably from 4 to 7, and in particular about 6.

Preferred embodiments of the TTS according to the invention which achieve the above-described active ingredient concentrations are listed as follows: $12^2$, $12^3$, $12^4$, $18^2$, $18^3$, $18^4$, $18^5$, $24^3$, $24^4$, $24^5$, $24^6$, $24^7$, $36^5$, $36^6$, $36^7$, $36^8$, $36^9$, $36^{10}$, $36^{11}$, $48^7$, $48^8$, $48^9$, $48^{10}$, $48^{11}$, $48^{12}$, $48^{13}$, $48^{14}$, $48^{15}$, $48^{16}$, $60^9$, $60^{10}$, $60^{11}$, $60^{12}$, $60^{13}$, $60^{14}$, $60^{15}$, $60^{16}$, $60^{17}$, $60^{18}$, $60^{19}$, $72^{12}$, $72^{13}$, $72^{14}$, $72^{15}$, $72^{16}$, $72^{17}$, $72^{18}$, $72^{19}$, $72^{20}$, $72^{21}$, $72^{22}$, $84^{14}$, $84^{15}$, $84^{16}$, $84^{17}$, $84^{18}$, $84^{19}$, $84^{20}$, $84^{21}$, $84^{22}$, $84^{23}$, $84^{24}$, $96^{19}$, $96^{20}$, $96^{21}$, $96^{22}$, $96^{23}$, $96^{24}$. Here, the duration of each administration interval in hours is specified first (e.g., "12") followed by, in superscript, the number of the TTSs according to the invention applied simultaneously, if applicable, in each case (e.g., "3"). Thus, "$24^2$" for example means the simultaneous administration in each case of two TTSs according to the invention for consecutive administration intervals of 24 h each.

Preferably, the TTS according to the invention is prepared for use according to the above-defined administration intervals. A further aspect of the invention provides a method for treating or preventing diseases of the central nervous system comprising the consecutive administration of multiple TTSs according to the invention while adhering to the above-defined administration intervals.

A person skilled in the art is aware that a particular ratio of administration duration to number of, if applicable, TTSs to be applied simultaneously on reduction of the number of TTSs to be applied simultaneously can be similarly achieved by an appropriate enlargement of the TTS, and vice versa. For instance, the pharmacological effect of a TTS having an active-ingredient-releasing area of, for example, 5 cm² is approximately double the pharmacological effect of an otherwise identical TTS having an active-ingredient-releasing area of 2.5 cm².

The active-ingredient-releasing area (active-ingredient containing contact area) of the TTS according to the invention is preferably in the range from 0.1 to 400 cm². In a preferred embodiment, the active-ingredient-releasing area of the TTS according to the invention is in the range of 10±9 cm², more preferably 10±7.5 cm², even more preferably 10±5 cm², most preferably 10±2.5 cm², and in particular 10±1 cm². In another preferred embodiment, the active-ingredient-releasing area of the TTS according to the invention is in the range of 20±9 cm², more preferably 20±7.5 cm², even more preferably 20±5 cm², most preferably 20±2.5 cm², and in particular 20±1 cm². In another preferred embodiment, the active-ingredient-releasing area of the TTS according to the invention is in the range of 25±20 cm², more preferably 25±15 cm², even more preferably 25±10 cm², most preferably 25±5 cm², and in particular 25±2.5 cm². In a further preferred embodiment, the active-ingredient-releasing area of the TTS according to the invention is in the range of 30±9 cm², more preferably 30±7.5 cm², even more preferably 30±5 cm², most preferably 30±2.5 cm², and in particular 30±1 cm². In another preferred embodiment, the active-ingredient-releasing area of the TTS according to the invention is in the range of 100±90 cm², more preferably 100±75 cm², even more preferably 100±50 cm², most preferably 100±25 cm², and in particular 100±10 cm². In a further preferred embodiment, the active-ingredient-releasing area of the TTS according to the invention is in the range of 200±90 cm², more preferably 200±75 cm², even more preferably 200±50 cm², most preferably 200±25 cm², and in particular 200±10 cm².

When the active-ingredient-releasing area is large enough, for example larger than, for example, 10 cm², it is possible, by covering part of the active-ingredient-containing area using an active-ingredient-impermeable protective layer, to reduce the actual active-ingredient-releasing area. For example, when the TTS according to the invention has a square active-ingredient-containing area of 6×6 cm, then 26 cm² of this area should be covered with an active-ingredient-impermeable layer in order to ensure an active-ingredient-releasing area of 10 cm². A person skilled in the art is aware that any transverse diffusion which occurs must be taken into account, more particularly in the case of substances which easily permeate into the adhesive-containing layer, and so the size of the protective layer may need to be adjusted.

In a preferred embodiment of the TTS according to the invention, the following active ingredient concentrations are achieved from the beginning in each case of the first administration:

after 24 h, no more than 50 ng/ml,
after 48 h, no more than 90 ng/ml,
after 60 h, no more than 110 ng/ml,
after 72 h, no more than 130 ng/ml,
after 96 h, no more than 150 ng/ml,
after 144 h, no more than 180 ng/ml,
after 192 h, no more than 195 ng/ml,
after 240 h, no more than 200 ng/ml, and
after 300 h, no more than 210 ng/ml.

Preferred ranges $B_1$ to $B_4$ of the active ingredient concentration are outlined in the following table:

| After | B1 | B2 | B3 | B4 |
|---|---|---|---|---|
| 24 h | 24.3 ng/ml ± 30% | 22.7 ng/ml ± 25% | 21.1 ng/ml ± 20% | 20.3 ng/ml ± 15% |
| 48 h | 43.8 ng/ml ± 30% | 40.9 ng/ml ± 25% | 38.0 ng/ml ± 20% | 36.5 ng/ml ± 15% |
| 60 h | 51.8 ng/ml ± 30% | 48.3 ng/ml ± 25% | 44.9 ng/ml ± 20% | 43.1 ng/ml ± 15% |
| 72 h | 58.7 ng/ml ± 30% | 54.7 ng/ml ± 25% | 50.8 ng/ml ± 20% | 48.9 ng/ml ± 15% |
| 96 h | 69.9 ng/ml ± 30% | 65.2 ng/ml ± 25% | 60.6 ng/ml ± 20% | 58.3 ng/ml ± 15% |
| 144 h | 84.9 ng/ml ± 30% | 79.2 ng/ml ± 25% | 73.6 ng/ml ± 20% | 70.8 ng/ml ± 15% |
| 192 h | 93.5 ng/ml ± 30% | 87.2 ng/ml ± 25% | 81.0 ng/ml ± 20% | 77.9 ng/ml ± 15% |
| 240 h | 98.3 ng/ml ± 30% | 91.7 ng/ml ± 25% | 85.2 ng/ml ± 20% | 81.9 ng/ml ± 15% |
| 300 h | 101.7 ng/ml ± 30% | 94.9 ng/ml ± 25% | 88.1 ng/ml ± 20% | 84.8 ng/ml ± 15% |

In a preferred embodiment, continuous intended use of the TTSs according to the invention achieves steady-state plasma concentrations of the active ingredient in the range from 70 to 150 ng/ml.

In a preferred embodiment of the TTS according to the invention, the active ingredient release rate thereof averaged over the administration interval is in the range from 0.2 to 2.0 mg/h. In a preferred embodiment, this averaged release rate is in the range of 0.7±0.5 mg/h, more preferably 0.7±0.4 mg/h, even more preferably 0.7±0.3 mg/h. In another preferred embodiment, this averaged release rate is in the range of 1.0±0.5 mg/h, more preferably 1.0±0.4 mg/h, even more preferably 1.0±0.3 mg/h. In a further preferred embodiment, this averaged release rate is in the range of 1.3±0.5 mg/h, more preferably 1.3±0.4 mg/h, even more preferably 1.3±0.3 mg/h. In another preferred embodiment, this averaged release rate is in the range of 1.5±0.5 mg/h, more preferably 1.5±0.4 mg/h, even more preferably 1.5±0.3 mg/h.

Preferably, the transdermally releasable amount of active ingredient present in a TTS according to the invention corresponds to at least a half daily dose, preferably to at least a complete daily dose, which is required for treating or preventing the disease in question of the central nervous system. The level of the required daily dose is known to a person skilled in the art.

In a preferred embodiment, the TTS according to the invention contains the corresponding dose for at least 1 day (transdermally releasable dose=single daily dose),
2 days (transdermally releasable dose=twice the daily dose),
3 days (transdermally releasable dose=three times the daily dose),
4 days (transdermally releasable dose=four times the daily dose),
5 days (transdermally releasable dose=five times the daily dose),
6 days (transdermally releasable dose=six times the daily dose), or
7 days (transdermally releasable dose=seven times the daily dose).

When the disease of the central nervous system is moderate to severe Alzheimer's disease, the preferred daily transdermally administered dose is about 20 mg (equivalent amount based on memantine hydrochloride). In the first weeks of the treatment, it may be advisable, however, to start with a lower daily transdermally administered dose, and to increase this dose over time until a value of about 20 mg is reached. For example, it is preferred for the daily transdermally administered dose to be about 5.0 mg in the first week, about 10 mg in the second week, about 15 mg in the third week, and about 20 mg continuously thereafter (equivalent amount based in each case on memantine hydrochloride).

Preferably, the area concentration of memantine or one of its physiologically compatible salts is at least 1.0 mg/cm$^2$, more preferably at least 5.0, 10 or 15 mg/cm$^2$, even more preferably at least 20, 25 or 30 mg/cm$^2$, most preferably at least 35, 40 or 50 mg/cm$^2$, and in particular at least 60 or 70 mg/cm$^2$.

In a preferred embodiment, the TTS according to the invention has a total layer thickness in the range from 50 to 4000 µm, more preferably from 100 to 2500 µm, even more preferably from 200 to 2000 µm, most preferably from 250 to 1500 µm, and in particular from 300 to 1200 µm.

The TTSs according to the invention are suitable for combating not only dementia but also further diseases of the central nervous system. These include acute neurodegenerative processes—for example in the case of trauma and stroke—chronic processes (besides the above-described Alzheimer's disease, these are, for example, Parkinson's disease and Huntington's disease [Huntington's chorea]) and also various symptomatic diseases connected with epilepsy, drug addictions, depressions and anxieties.

A further aspect of the invention provides a pack unit comprising at least two different types of the above-described TTS according to the invention which preferably differ in the daily releasable dose (memantine or one of its physiologically compatible salts) contained therein. Preference is given to there being present at least 2, more preferably at least 3, and in particular at least 4, different TTS types having different daily releasable doses, and TTS types having the same daily releasable dose can preferably be represented more than once (multiple types of the same kind).

In a preferred embodiment, the pack unit according to the invention comprises as many TTSs as required so that daily releasable maximum dose can be achieved starting from a daily releasable initial dose by means of stepwise increases (titration). Preferably, this maximum dose is achieved over 2, 3 or 4 steps, and each step can comprise similar or different periods, single or multiple application intervals. An application interval in this context is the period over which the advised daily dose to be administered transdermally is actually releasable when the TTS in question is used as intended. When an application interval is, for example, 48 h, then the TTS must ensure that the daily dose in question to be administered transdermally is actually releasable from the TTS over this period.

In a preferred embodiment, the application intervals correspond to the administration intervals described above in connection with the active ingredient concentration.

The invention further provides a kit for treating or preventing diseases of the central nervous system, comprising at least one dosage form for the initial nontransdermal, preferably oral or parenteral, administration of memantine or one of its physiologically compatible salts and at least one TTS according to the invention.

A further aspect of the invention provides for the use of memantine or of a physiologically compatible salt or prodrug for producing an above-described TTS for treating or preventing diseases of the central nervous system. Preferably, the disease of the central nervous system is selected from the group consisting of dementia, more particularly Alzheimer's disease, trauma, stroke, Parkinson's syndrome, Huntington's syndrome, epilepsy, drug addiction, depression, and anxiety states.

The following examples serve to explain the invention, but are not to be understood to be restrictive.

Example 1

A TTS in the form of an active-ingredient-containing patch having the following composition was produced:

| | |
|---|---|
| Memantine base | 6.36% by weight |
| Triglyceride of medium chain length (e.g., MIGLYOL 812) | 25.42% by weight |
| Acrylate-vinyl acetate copolymer (e.g., DUROTAK 2516) | 68.22% by weight |
| Active-ingredient-containing area | 10 cm$^2$ |
| Active ingredient content (calculated as base) | 11.0 mg |

In addition, a metering solution of memantine (free base) and MIGLYOL 812 having the following mixing ratio was prepared.

| | |
|---|---|
| Memantine base | 20.00% by weight |
| Triglyceride of medium chain length (e.g., MIGLYOL 812) | 80.00% by weight |

The appropriate acrylate, for example DUROTAK® 2516, is coated onto a suitable release liner (e.g., polyethylene terephthalate sheet, PET), dried, and laminated with a suitable occlusive backing layer (1st layer). Subsequently, a 2nd layer made of, for example, DUROTAK® 2516 as described above is produced, but not laminated with a suitable backing layer. Instead, a suitable fabric, for example long-fiber paper LF26, of a defined size (e.g., 10 cm²) is applied to the dried acrylate layer, and an appropriate amount of the metering solution is metered onto the suitable fabric. The 1st layer is laminated onto the 2nd layer containing the fabric after removal of the release liner. After the TTSs have been punched out (such that the fabric is centered), they are packed in a suitable material, preferably PET.

Example 2

Based on example 1, eight different TTSs in the form of active-ingredient-containing patches (drug in adhesive) of the following compositions were produced:

| | % by weight | | | | | | | |
|---|---|---|---|---|---|---|---|---|
| | 2-1 | 2-2 | 2-3 | 2-4 | 2-5 | 2-6 | 2-7 | 2-8 |
| Memantine base | 6.00 | 6.00 | — | — | — | — | — | — |
| Memantine HCl | — | — | 40.00 | 10.00 | 30.00 | 30.00 | 30.00 | 30.00 |
| CaO | — | — | — | — | 7.50 | 7.50 | 7.50 | 7.50 |
| Na caprylate | — | — | 10.00 | — | — | — | — | — |
| Na ethanolate | — | — | — | 7.00 | — | — | — | — |
| Basic methacrylate copolymer (e.g., EUDRAGIT® E 100) | — | — | 20.00 | — | — | — | — | — |
| Poly(butyl-methacrylate, methyl-methacrylate) (e.g., PLASTOID® B) | 2.00 | 2.00 | — | — | — | — | — | — |
| Acrylate-vinyl acetate copolymer (e.g., DUROTAK® 2516) | 92.00 | — | — | 83.00 | — | — | — | — |
| Acrylate-vinyl acetate copolymer (e.g., DUROTAK® 2287) | — | 92.00 | 30.00 | — | — | — | — | — |
| Poly-isobutylene | — | — | — | — | 62.50 | — | — | — |
| Neutral poly-acrylate (e.g., DUROTAK® 900A) | — | — | — | — | — | 62.50 | — | — |
| Neutral poly-acrylate (e.g., DUROTAK® 9301) | — | — | — | — | — | — | 62.50 | — |
| Neutral poly-acrylate (e.g., GMS 3083) | — | — | — | — | — | — | — | 62.50 |
| Active-ingredient-containing area | 30 cm² | 30 cm² | 30 cm² | 30 cm² | 10 cm² | 10 cm² | 10 cm² | 10 cm² |
| Active ingredient content (calculated as base) | 39.8 mg | 48.9 mg | 98.2 mg | 27.5 mg | 24.7 mg | 23.4 mg | 25.6 mg | 24.8 mg |

The appropriate amount of memantine hydrochloride or memantine base is initially charged, and suspended with or, for the base, dissolved in about ⅓ of the amount—based on the amount of active ingredient—with an organic solvent (e.g., ethyl acetate). After addition of the appropriate amount of a suitable acrylate, stirring is carried out in order to ensure a homogeneous distribution of the active ingredient in the polymer.

Subsequently, the appropriate further raw materials (PLASTOID® B for 2-1 and 2-2 and Na caprylate and EUDRAGIT® E 100 for 2-3 and Na ethanolate for 2-4 and CaO for 2-5 to 2-8) are added to the mass with stirring, and stirred further until a homogeneous mass is obtained. After coating onto a suitable release liner (e.g., polyethylene terephthalate sheet, PET), the laminate is dried and laminated onto a suitable occlusive backing layer. Here, in order to achieve the necessary thickness or active ingredient load, three layers were laminated together (each with a suitable fabric (e.g., PET nonwoven fabric) for stabilization between the acrylate layers) for example 2-1, and this was three layers without fabric for 2-2 and 2-3, and two layers for 2-4, and one layer for 2-5 to 2-8. After the TTSs have been punched out, they are packed in a suitable material, preferably PET.

Figure 3:
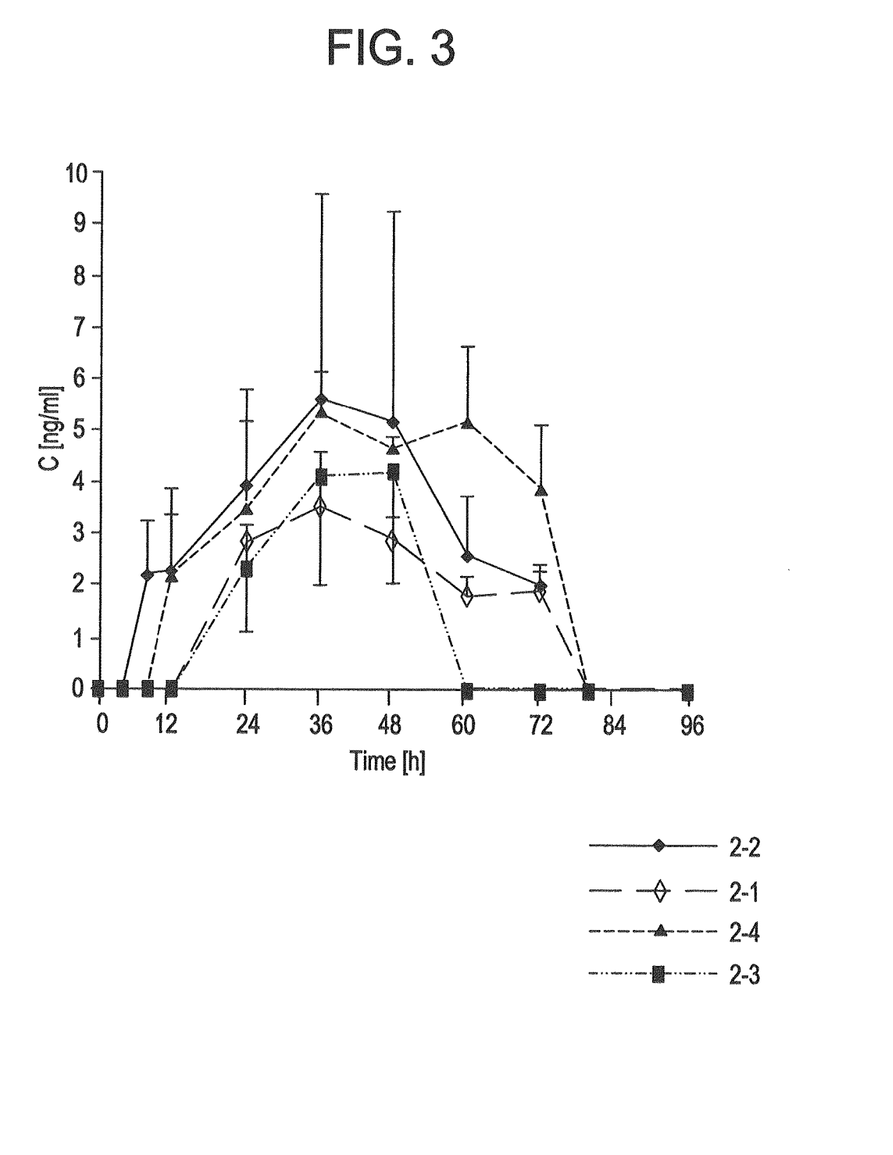
FIG. 3 illustrates an exemplary plasma concentration of memantine after three days of administration (removal of the TTSs after 72 h).

The TTSs according to the invention as per examples 2-1, 2-2, 2-3 and 2-4 were tested in vivo (rabbits). The plasma concentrations of memantine after three days of administration (removal of the TTSs after 72 h) are shown in FIG. 3.

Example 3

The TTSs as per example 2-7 were tested in a clinical human study. A group of subjects (group 1) received 3 active-ingredient-containing patches having an active ingredient content of, in each case, 24.0 mg of memantine calculated as base. After 24 hours, one of the patches was removed. After a further 24 hours, a further patch was removed. After a further 24 hours, the last patch was removed. Another group of subjects (group 2) received 2 active-ingredient-containing patches having an active ingredient content of, in each case, 24.0 mg of memantine calculated as base, for 48 hours.

The pharmacokinetic parameters were determined from the plasma concentrations measured and are outlined in the following table:

|  |  | $C_{max}$ [ng/ml] | $t_{max}$ [h] | $t_{lag}$ [h] | $t_{last}$ [h] | $AUC_{0-t}$ [h ng/ml] | $AUC_{0-8}$ [h ng/ml] | $t_{1/2,z}$ [h] |
|---|---|---|---|---|---|---|---|---|
| Group 1 | N | 3 | 3 | 3 | 3 | 3 | 3 | 3 |
|  | Mean | 17.1 | 32.0 | 1.33 | 240 | 1711 | 1794 | 49.8 |
|  | Median | 17.6 | 36.0 | 0.00 | 240 | 1758 | 1839 | 48.1 |
|  | S.D. | 2.64 | 6.93 | 2.31 | 0.00 | 260 | 262 | 3.65 |
|  | C.V. [%] | 15.5 | 21.7 | 173 | 0.00 | 15.2 | 14.6 | 7.34 |
| Group 2 | N | 3 | 3 | 3 | 3 | 3 | 3 | 3 |
|  | Mean | 11.5 | 36.0 | 1.33 | 240 | 1156 | 1236 | 56.9 |
|  | Median | 12.2 | 36.0 | 0.00 | 240 | 1230 | 1306 | 57.0 |
|  | S.D. | 1.59 | 0.00 | 2.31 | 0.00 | 166 | 173 | 1.80 |
|  | C.V. [%] | 13.8 | 0.00 | 173 | 0.00 | 14.4 | 14.0 | 3.17 |
|  | Ratio Gr. 1/Gr. 2 | 1.49 | 0.89 | 1.00 | 1.00 | 1.48 | 1.45 | 0.88 |

The residual contents of active ingredient in the TTS after the administration were likewise determined and are outlined in the following table for all 6 subjects:

| Subject | TTS | Memantine residual content 10 cm² TTS [mg/10 cm²] |
|---|---|---|
| 1 | 1 | 16.569 |
|  | 2 | 15.152 |
|  | 3 | 14.257 |
|  | Mean value | 15.326 |
|  | Standard deviation | 1.1656 |
| 2 | 1 | 17.058 |
|  | 2 | 15.112 |
|  | 3 | 13.500 |
|  | Mean value | 15.223 |
|  | Standard deviation | 1.7816 |
| 3 | 1 | 17.412 |
|  | 2 | 16.865 |
|  | 3 | 16.404 |
|  | Mean value | 16.894 |
|  | Standard deviation | 0.5046 |
| 4 | 1 | 16.193 |
|  | 2 | 15.858 |
|  | Mean value | 16.026 |
|  | Standard deviation | 0.2369 |
| 5 | 1 | 15.330 |
|  | 2 | 15.356 |
|  | Mean value | 15.343 |
|  | Standard deviation | 0.0184 |
| 6 | 1 | 14.810 |
|  | 2 | 15.159 |
|  | Mean value | 14.985 |
|  | Standard deviation | 0.2468 |

That which is claimed:

1. Transdermal therapeutic systems comprising memantine as an active ingredient, said memantine present as a free base or as a physiologically compatible salt or prodrug,
    said transdermal therapeutic systems including at least one transdermal therapeutic system comprising
    a backing layer impermeable to active ingredient;
    a fabric or paper stabilizer;
    at least one active-ingredient-containing layer having an area concentration of memantine of at least 15 mg/cm² to 70 mg/cm² and which further comprises a storage material into which the active ingredient is introduced;
    a $t_{max}$ of 30 h to 48 h;
    and wherein either consecutive or staggered administration of one or more of the transdermal therapeutic system at a time for administration intervals each lasting 12 h to 168 h independently of one another, for achieving active ingredient concentrations in a blood plasma of an individual requiring treatment, achieves, in the blood plasma, active ingredient concentrations from a beginning of the administration of a first of one or more of said transdermal therapeutic system as follows:
after 24 h, at least 14 ng/ml to no more than 50 ng/ml,
after 48 h, at least 27 ng/ml to no more than 90 ng/ml,
after 60 h, at least 32 ng/ml to no more than 110 ng/ml,
after 72 h, at least 37 ng/ml to no more than 130 ng/ml,
after 96 h, at least 44 ng/ml to no more than 150 ng/ml,
after 144 h, at least 54 ng/ml to no more than 180 ng/ml,
after 192 h, at least 60 ng/ml to no more than 195 ng/ml,
after 240 h, at least 63 ng/ml to no more than 200 ng/ml, and
after 300 h, at least 65 ng/ml to no more than 210 ng/ml,
and said transdermal therapeutic systems have a memantine pharmacokinetic delay, $t_{lag}$, of not more than 6 hours.

2. The transdermal therapeutic systems as claimed in claim 1, wherein each administration interval further comprising a duration of the administration interval in h and a number of simultaneously administered transdermal therapeutic systems whereby said duration in h divided by said number of the simultaneously administered transdermal therapeutic systems is in a range from 3 to 8.

3. The transdermal therapeutic systems as claimed in claim 1, wherein the active ingredient concentrations are achieved upon administering one transdermal therapeutic system per administration interval or upon administering, simultaneously, multiple transdermal therapeutic systems per administration interval.

4. The transdermal therapeutic systems as claimed in claim 1, wherein the active ingredient concentrations are achieved when each administration interval is not more than 72 h.

5. The transdermal therapeutic systems as claimed in claim 1, wherein
the active ingredient has a release rate of from 0.2 to 2.0 mg/h thereof averaged over the administration interval; and/or
the memantine pharmacokinetic delay $t_{lag}$ is not more than 2.33 h.

6. The transdermal therapeutic systems as claimed in claim 1, wherein the storage material
comprises a matrix which is based on a polymeric material and in which the active ingredient is dissolved or distributed as a microdispersion; and/or
comprises a polyacrylate- or polysilicone-based polymeric material; and/or
is a lipogel which contains from 10 to 50% by weight of active ingredient.

7. The transdermal therapeutic systems as claimed in claim 1, wherein the active ingredient consists of memantine, the storage material does not comprise a cellulose derivative, more than one transdermal therapeutic systems is administered at a time and said system does not comprise one or more of silicone or tackifier.

8. The transdermal therapeutic systems as claimed in claim 1, wherein said transdermal therapeutic systems for administering memantine further comprises administering a daily dosage of memantine, administered in a first treatment week, a second treatment week, and a third treatment week, whereby administration during the first treatment week comprise 25% of the daily dosage; administration during the second treatment week comprise 50% of the daily dosage; and administration during the third treatment week comprise 75% of the daily dosage; and said transdermal therapeutic systems thereafter comprise 100% of the daily dosage.

9. A pack unit comprising transdermal therapeutic systems as claimed in claim 1, wherein said pack unit comprises at least two different transdermal therapeutic systems which differ in their releasable dosage, wherein a daily releasable maximum dose is achieved starting from a lower daily releasable initial dose that is increased stepwise over 2, 3 or 4 steps, with each step comprising single or multiple application intervals.

10. The transdermal therapeutic systems as claimed in claim 1, wherein said storage material within said active-ingredient-containing layer is acrylate thereby forming acrylate active-ingredient-containing layers and (i) said memantine is in a metering solution metered onto fabric; (ii) the transdermal therapeutic system comprises more than one active-ingredient containing layers or (iii) the transdermal therapeutic system comprises more than one active-ingredient-containing layer and the fabric or paper stabilizer is present between the acrylate active-ingredient-containing layers for stabilization.

11. A kit for treating or preventing central nervous system diseases comprising at least one nontransdermal dosage form wherein said nontransdermal dosage form is used to administer memantine or one of its physiologically compatible salts and the transdermal therapeutic system as claimed in claim 1.

12. The transdermal therapeutic systems as claimed in claim 1, wherein the area concentration of memantine or one of its physiologically compatible salts is 30 mg/cm^2 to 70 mg/cm^2.

13. The transdermal therapeutic systems as claimed in claim 1, wherein said transdermal therapeutic system administers memantine in the absence of polydimethylsiloxane.

14. The transdermal therapeutic systems as claimed in claim 1, wherein the active-ingredient-containing layer(s) comprise 30 to 50% memantine, based on the weight of the active-ingredient-containing layer and exhibit a $t_{max}$ of 32 h to 48 h.

15. Transdermal therapeutic systems comprising memantine as an active ingredient,
said transdermal therapeutic systems including at least one transdermal therapeutic system comprising
a backing layer impermeable to active ingredient;
a fabric or paper stabilizer
at least one active-ingredient-containing layer comprising 30 to 50% memantine, based on the weight of the active-ingredient-containing layer, and which further comprises a storage material into which the active ingredient is introduced;
a $t_{max}$ of 30 h to 48 h;
and wherein consecutive or staggered administration of one or more of the transdermal therapeutic system at a time for administration intervals each lasting 12 h to 168 h independently of one another, for achieving active ingredient concentrations in a blood plasma of an individual requiring treatment, achieves, in the blood plasma, active ingredient B concentrations from a beginning of the administration of a first of one or more of said transdermal therapeutic system as follows:
after 24 h, at least 14 ng/ml to no more than 50, ng/ml,
after 48 h, at least 27 ng/ml to no more than 90 ng/ml,
after 60 h, at least 32 ng/ml to no more than 110 ng/ml,
after 72 h, at least 37 ng/ml to no more than 130 ng/ml,
after 96 h, at least 44 ng/ml to no more than 150 ng/ml,
after 144 h, at least 54 ng/ml to no more than 180 ng/ml,
after 192 h, at least 60 ng/ml to no more than 195 ng/ml,
after 240 h, at least 63 ng/ml to no more than 200 ng/ml, and after 300 h, at least 65 ng/ml to no more than 210 ng/ml, and said transdermal therapeutic systems have a memantine pharmacokinetic delay, $t_{lag}$, of not more than 6 hours wherein the active ingredient is present as a physiologically compatible salt or prodrug.

16. The transdermal therapeutic systems as claimed in claim 15, wherein the storage material is a storage material polymer that (i) is pressure-sensitively adhesive and (ii) consists of a single polymer and the active-ingredient-containing layer additionally comprises at least one basic material and the transdermal therapeutic system does not comprise a separate adhesive layer.

17. The transdermal therapeutic systems as claimed in claim 16, wherein the at least one basic material is selected from the group consisting of polymers having basic side groups, organic bases and inorganic bases.

18. The transdermal therapeutic systems as claimed in claim 17, wherein the at least one basic material is selected from the group consisting of acrylate-based polymers which have aminoalkyl side groups; inorganic oxides or hydroxides; organic amines or salts thereof; alkali metal alcoholates or carboxylates or alkaline earth metal alcoholates or carboxylates.

19. The transdermal therapeutic systems as claimed in claim 16, wherein the active-ingredient-containing layer comprises from 20 to 70% by weight of storage material, and from 30% to 50% by weight of active ingredient, based on the active-ingredient-containing layer total weight.

20. A method for treating or preventing a central nervous system disease comprising applying the transdermal therapeutic systems as claimed in claim 16 including memantine or a physiologically compatible salt or prodrug thereof.

21. The method as claimed in claim 20, wherein the central nervous system disease is selected from the group consisting of dementia, trauma, stroke, Parkinson's syndrome, Huntington's syndrome, epilepsy, drug addiction, depression, and anxiety states.

22. The transdermal therapeutic systems as claimed in claim 16, wherein said transdermal therapeutic system further comprise a release liner.

23. The transdermal therapeutic systems as claimed in claim 19, wherein the active-ingredient-containing layer further comprises from 5 to 40% by weight of basic material, based on the active-ingredient-containing layer total weight.

* * * * *